US010675463B2

(12) United States Patent
Masuda et al.

(10) Patent No.: US 10,675,463 B2
(45) Date of Patent: Jun. 9, 2020

(54) DYSURIA TREATMENT DEVICE

(71) Applicant: OTSUKA TECHNO CORPORATION, Naruto-shi, Tokushima (JP)

(72) Inventors: Tetsuya Masuda, Naruto (JP); Nobuo Tsukui, Naruto (JP)

(73) Assignee: OTSUKA TECHNO CORPORATION, Tokushima (JP)

(*) Notice: Subject to any disclaimer, the term of this patent is extended or adjusted under 35 U.S.C. 154(b) by 0 days.

(21) Appl. No.: 16/333,465

(22) PCT Filed: Jul. 2, 2018

(86) PCT No.: PCT/JP2018/025112
§ 371 (c)(1),
(2) Date: Mar. 14, 2019

(87) PCT Pub. No.: WO2019/021753
PCT Pub. Date: Jan. 31, 2019

(65) Prior Publication Data
US 2019/0262606 A1  Aug. 29, 2019

(30) Foreign Application Priority Data
Sep. 6, 2017 (JP) .................. 2017-171382

(51) Int. Cl.
*A61N 1/36* (2006.01)
*A61B 5/0488* (2006.01)
(Continued)

(52) U.S. Cl.
CPC ...... *A61N 1/36007* (2013.01); *A61B 5/04882* (2013.01); *A61B 5/202* (2013.01);
(Continued)

(58) Field of Classification Search
CPC ............. A61N 1/36; A61N 1/372; A61N 1/05
(Continued)

(56) References Cited

U.S. PATENT DOCUMENTS

2009/0259216 A1  10/2009  Drew et al.
2012/0197339 A1   8/2012  Takagi et al.
2016/0045747 A1*  2/2016  Jiang .................. A61N 1/37241
                                              607/40

FOREIGN PATENT DOCUMENTS

CN   102049095 A    5/2011
CN   106139405 A   11/2016
(Continued)

OTHER PUBLICATIONS

Decision to Grant a Patent issued in the corresponding Japanese patent application No. 2018-535429, dated Jan. 24, 2019.
(Continued)

*Primary Examiner* — Jon Eric C Morales
(74) *Attorney, Agent, or Firm* — Birch, Stewart, Kolasch & Birch, LLP

(57) ABSTRACT

Provided is a urination disorder treatment device which easily confirms with high accuracy whether it is appropriately used or not.
In the urination disorder treatment device, a control portion compares a stimulation pulse 58 by a pair of body-surface electrode pads with a detection pulse 60 of a toe to judge whether a nerve passing through the sacral bone or the vicinity of the sacral bone is appropriately stimulated by the stimulation pulse 58 or not. Further, the detection pulse 60 is generated by reactions of the tibial nerve and/or the peroneal nerve extended up to the tiptoe which are connected to the nerve passing through the sacral bone or the vicinity of the sacral bone by way of the ischiadic nerve.

5 Claims, 12 Drawing Sheets

(51) Int. Cl.
*A61N 1/04* (2006.01)
*A61B 5/20* (2006.01)
*A61B 5/04* (2006.01)

(52) U.S. Cl.
CPC ............ *A61N 1/0456* (2013.01); *A61N 1/36* (2013.01); *A61B 5/04001* (2013.01); *A61N 1/36021* (2013.01)

(58) Field of Classification Search
USPC .................................................... 607/40, 41
See application file for complete search history.

(56) References Cited

FOREIGN PATENT DOCUMENTS

| CN | 107073258 A | 8/2017 |
|----|---|---|
| JP | 2002-200178 A | 7/2002 |
| JP | 4839457 B2 | 12/2011 |
| JP | 2017-523868 A | 8/2017 |
| JP | 6488498 B1 | 3/2019 |
| WO | WO 2011/033750 A1 | 3/2011 |
| WO | WO 2016/025913 A1 | 2/2016 |

OTHER PUBLICATIONS

International Search Report, issued in PCT/JP2018/025112, PCT/ISA/210, dated Oct. 2, 2018.
Written Opinion of the International Searching Authority, issued in PCT/JP2018/025112, PCT/ISA/237, dated Oct. 2, 2018.

\* cited by examiner

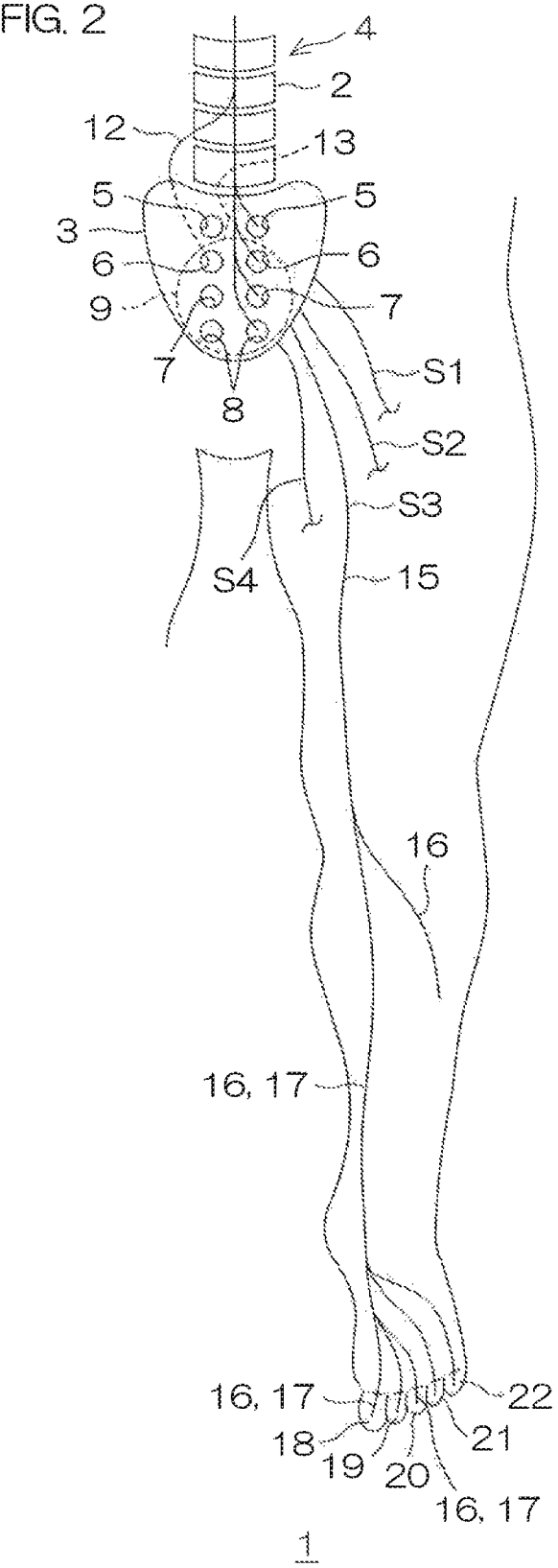

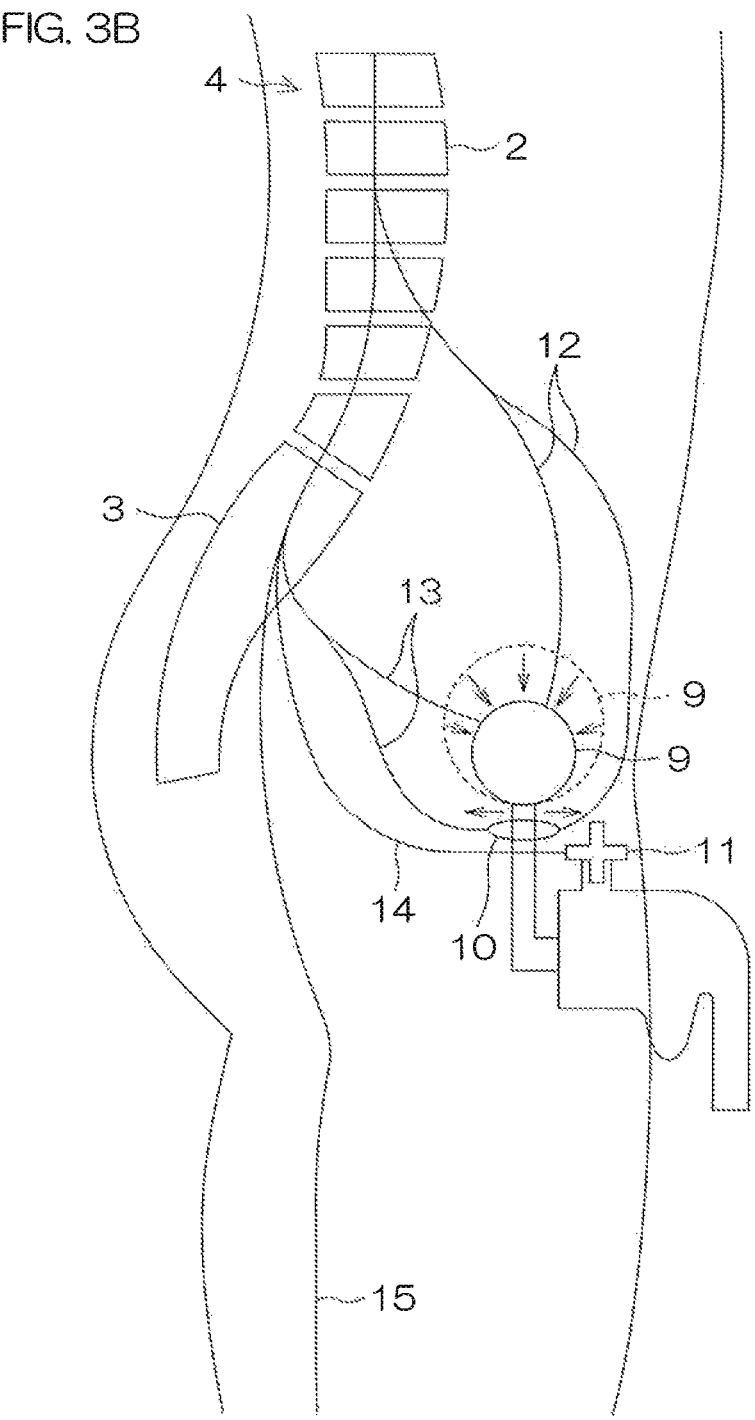

FIG. 13
Stimulation pulse
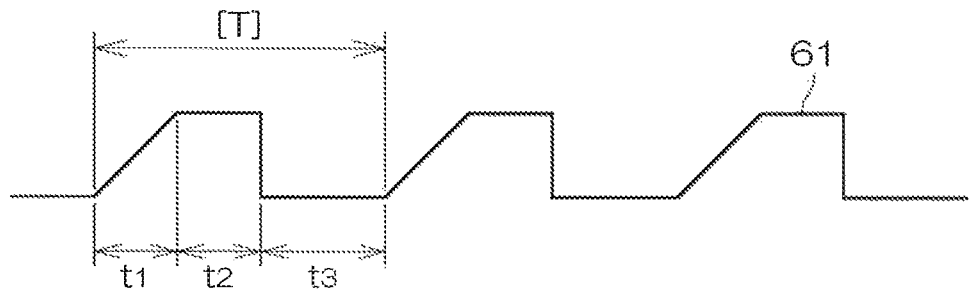
Detection pulse
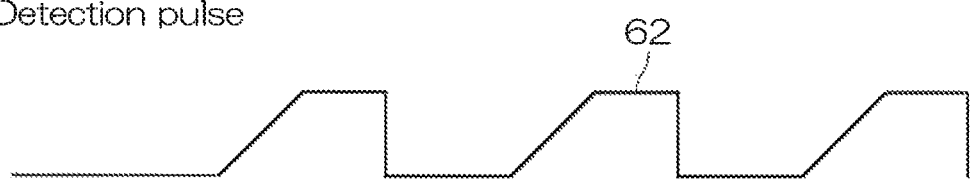
FIG. 14
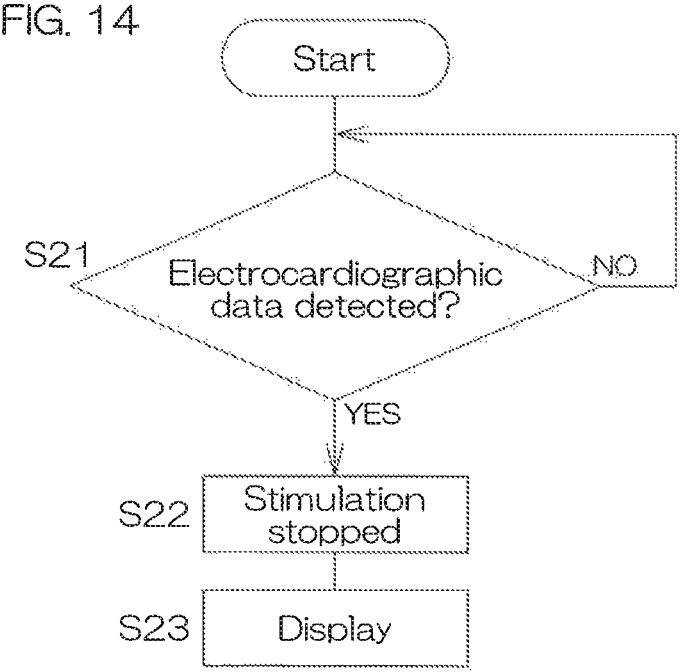

DYSURIA TREATMENT DEVICE

TECHNICAL FIELD

The present invention relates to a device which is used for treating urination disorders.

BACKGROUND ART

There have been so far proposed various types of devices for treating urination disorders.

For example, Patent Literature 1 has disclosed a pelvic viscera dysfunction or a pain treatment device which is provided with a CPU (central processing unit), an emergency stimulation switch connected to the CPU, a manual stimulation maximum value setting dial connected to the CPU, a stimulation frequency changeover switch, an output portion having a D/A converter, and electrodes including an indifferent electrode and a different electrode (stimulation electrode) to which an electrical stimulation is applied. In this device, to the pelvic splanchnic nerve and the pudic nerve which are a second to a fourth sacral nerve of the human body, an electrical stimulation is given to excite these nerves from the skin immediately above a second to a fourth posterior sacral foramina, and a urination disorder is treated in this manner.

Further, for example, Patent Literature 2 has disclosed underwear for wearing an electrode device which is provided with a sacral region surface stimulating electrode that is arranged with an electrode portion composed of a metal sheet and an adhesive pad attached thereto as well as a code which is connected to the metal sheet.

CITATION LIST

Patent Literature

Patent Literature 1: Japanese Patent No. 4839457 Patent Literature 2: Japanese Patent Application Publication No. 2002-200178

SUMMARY OF INVENTION

Technical Problem

The above-described device is unable to give sufficient electrical stimulation to a target nerve if not used by attaching an electrode to a predetermined position on the skin, thus resulting in reduction of treatment effects. However, the attachment is slightly varied depending on various factors such as shape, physical constitution, etc., of a user, making it difficult to judge whether the device is appropriately attached or not.

An object of the present invention is to provide a urination disorder treatment device which easily confirms with high accuracy whether the device is appropriately used or not.

Solution to Problem

A urination disorder treatment device of the present invention includes a pair of application electrodes which are disposed at the back of a sacral bone of a person to be treated to supply an electrical stimulation signal from the back of the sacral bone, a signal supply source from which the pair of application electrodes supply the stimulation signal, a detection electrode which is disposed on a surface of a toe of a person to be treated to detect a biological signal of the toe which is generated in response to the stimulation signal, a measurement portion which is connected to the detection electrode to measure electromyographic data of the toe based on the biological signal of the toe of a person to be treated, a control portion which is connected to the measurement portion to control supply of the stimulation signal to the sacral bone by the pair of application electrodes and also compares signal data of the stimulation signal with electromyographic data of the toe to judge whether a nerve which passes through the sacral bone or the vicinity of the sacral bone is appropriately stimulated by the stimulation signal or not, and a display portion which informs a person to be treated of a judgment result by the control portion, in which the biological signal of the toe to be detected is generated by reaction of a tibial nerve and/or a peroneal nerve extended up to the tiptoe which are connected to a nerve passing through the sacral bone or the vicinity of the sacral bone by way of an ischiadic nerve.

In the urination disorder treatment device of the present invention, the control portion may judge an appropriate stimulation from the stimulation signal to the sacral bone by comparing a frequency pattern of a pulse wave of the signal data of the stimulation signal with a frequency pattern of a pulse wave of the electromyographic data thereof.

Advantageous Effects of Invention

The urination disorder treatment device of the present invention is able to easily confirm whether a stimulation signal is appropriately transmitted from the application electrodes to the nerve passing through the sacral bone or the vicinity of the sacral bone based on the electromyographic data of the toes. Further, the toes are terminal portions of the tibial nerve and the peroneal nerve and, therefore, noise is less likely to enter as compared with a case where a biological signal is detected at other parts of the body, and a biological signal occurring in response to the stimulation signal can be clearly detected. Further, since the toes are different from a site such as the perineum to which it is difficult to attach an electrode, the electrode can be easily attached thereto. As a result, it is possible to confirm in a simplified manner with high accuracy whether the urination disorder treatment device is appropriately used or not (whether the stimulation signal is appropriately transmitted or not).

BRIEF DESCRIPTION OF DRAWINGS

FIG. 2 is a rear view of the human body for describing innervation of urination.

FIG. 3B is a drawing for describing a mechanism of urination.

FIG. 13 is a drawing which describes one example of frequency patterns of the stimulation pulse and the detection pulse.

FIG. 14 is a flow chart which describes one example of processing related to stimulation influence elimination on the heart executed by the control portion.

DESCRIPTION OF EMBODIMENTS

Hereinafter, modes of executing the present invention will be described in detail with reference to attached drawings.

Figure 1:
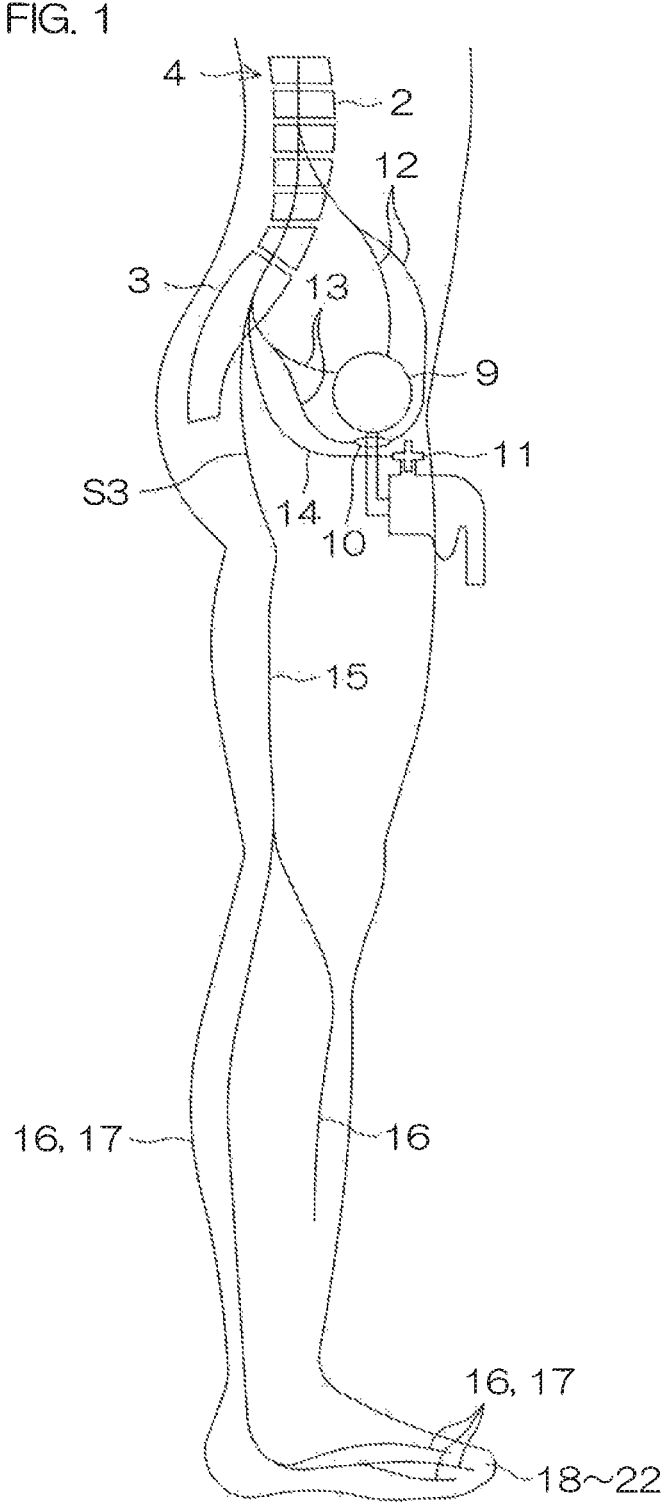
FIG. 1 is a side sectional view of the human body for describing innervation of urination.
Figure 3A:
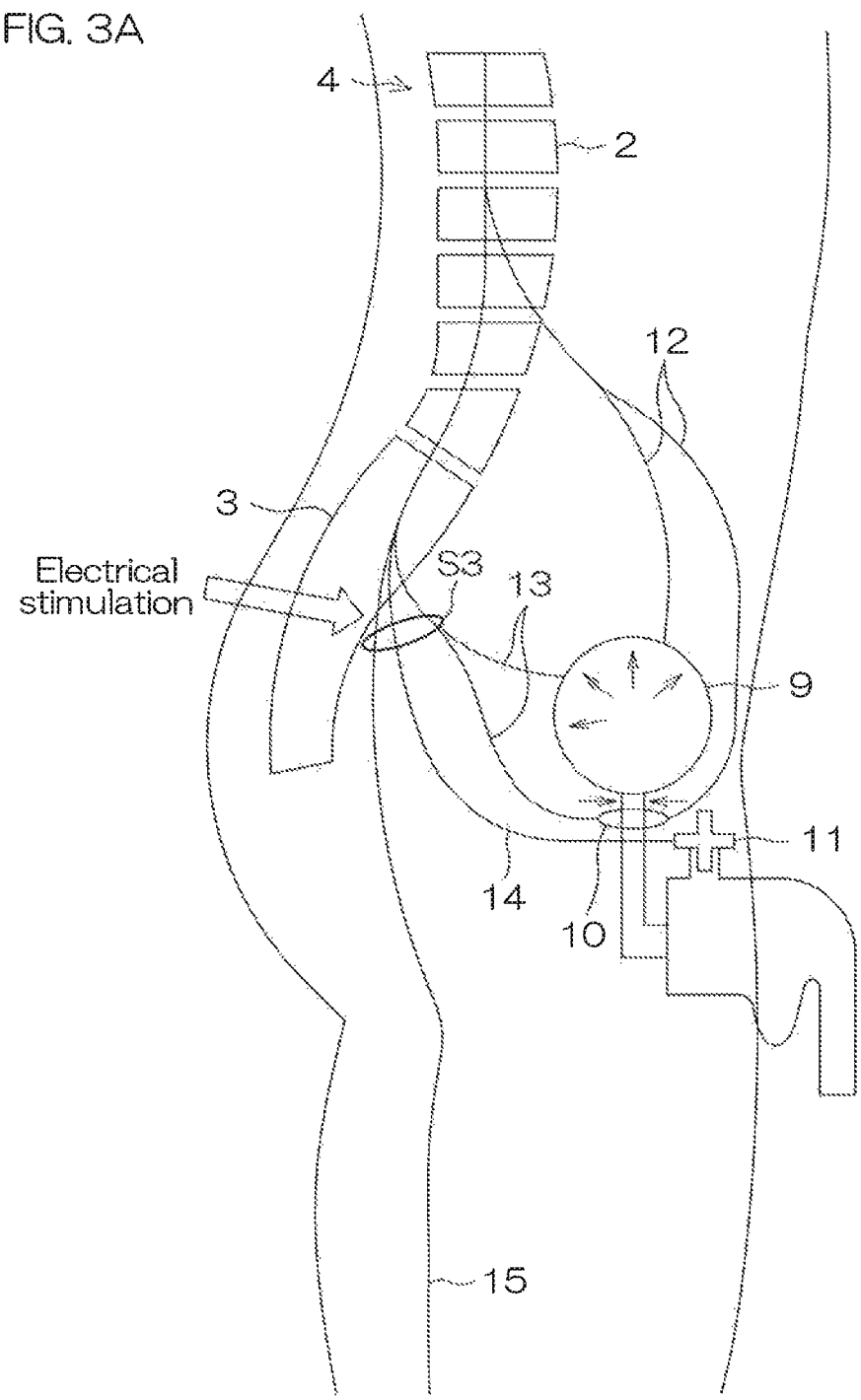
FIG. 3A is a drawing for describing a mechanism of urination.

FIG. 1 is a side sectional view of a human body 1 for describing innervation of urination. FIG. 2 is a rear view of the human body 1 which describes innervation of urination. FIG. 3A and FIG. 3B are each a drawing which describes a mechanism of urination. In FIG. 1 to FIGS. 3A and 3B, of various sites of the human body 1, there are shown only sites which are necessary for describing treatment by using a urination disorder treatment device 31 according to a preferred embodiment of the present invention, with a description of other sites being omitted here.

The human body 1 has a vertebral column 4 which includes a lumbar vertebra 2, a sacral bone 3 and others. The sacral bone 3 assumes a substantially inverted triangular shape, normally having four foramina on both sides symmetrically, from above, a first sacral foramen 5, a second sacral foramen 6, a third sacral foramen 7, and a fourth sacral foramen 8.

Further, the human body 1 has a bladder 9, an internal urethral sphincter 10 and an external urethral sphincter 11 as sites (organs and muscles) involved in collecting and discharging urine. These sites of 9 to 11 are neurologically controlled to collect and discharge urine in the human body 1.

In the human body 1, nerves mainly contributing to collection and discharge of urine are a hypogastric nerve (sympathetic nerve) 12, a pelvic nerve (parasympathetic nerve) 13 and a pudic nerve (somatic nerve) 14.

The hypogastric nerve 12 contributes to suppression of urination (urine collection) and is connected to the bladder 9 and the internal urethral sphincter 10. The pelvic nerve 13 contributes to the initiation of urination and connected to the bladder 9 and the internal urethral sphincter 10. The pudic nerve 14 is connected to the external urethral sphincter 11.

As shown in FIG. 3A, in the human body 1, first, the bladder 9 (detrusor muscle) is relaxed by a signal from the hypogastric nerve 12, by which urine can be easily collected in the bladder 9 and the internal urethral sphincter 10 is also contracted. Thereby, urine is prevented from being discharged but collected in the bladder 9. On the other hand, as shown in FIG. 3B, the bladder 9 (detrusor muscle) is contracted by a signal from the pelvic nerve 13, and the internal urethral sphincter 10 is also relaxed. Thereby, urine is discharged outside the bladder 9. Then, the external urethral sphincter 11 as a voluntary muscle is relaxed by a command from the brain of the human body 1 (one's own volition) by way of the pudic nerve 14 which is a somatic nerve, and an abdominal muscle pressure is applied to discharge urine.

As described above, if the hypogastric nerve 12 and the pelvic nerve 13 are both normally engaged in activity to appropriately contract and relax the bladder 9 and the internal urethral sphincter 10, urine is collected or discharged normally. However, for example, when the hypogastric nerve 12 is activated at a lower level or the pelvic nerve 13 is activated excessively, the bladder 9 is more likely to contract and the internal urethral sphincter 10 is more likely to relax. As a result, urine is more easily collected in the bladder 9, which may trigger onset of a urination disorder such as a urine collection failure (overactive bladder).

Thus, in the preferred embodiment, as shown in FIG. 3A, an electrical stimulation signal is given to the skin on the sacral bone 3 from the back of the sacral bone 3, thereby stimulating the sacral plexus. More specifically, as shown in FIG. 2, there are stimulated a first sacral nerve S1 which passes through the first sacral foramen 5, a second sacral nerve S2 which passes through the second sacral foramen 6, a third sacral nerve S3 which passes through the third sacral foramen 7 and a fourth sacral nerve S4 which passes through the fourth sacral foramen 8. Thereby, for example, as shown in FIG. 3A, the third sacral nerve S3 is stimulated to suppress innervation which causes the bladder 9 to be contracted by the pelvic nerve 13. Further, this electrical stimulation is also sent to the hypogastric nerve 12, thereby accelerating innervation which allows the bladder 9 to be relaxed by the hypogastric nerve 12. As a result, suppression of the pelvic nerve 13 is well-balanced with acceleration of the hypogastric nerve 12, by which the bladder 9 is appropriately relaxed to improve an overactive bladder.

Next, the above-described electrical stimulation is also transmitted to the nerves present at sites other than the buttocks and peripheries thereof at which the sacral plexus is found. For example, as shown in FIG. 2, some of the third sacral nerves S3 partially descend the femur as an ischiadic nerve 15 and finally are divided into a peroneal nerve 16 and a tibial nerve 17. The peroneal nerve 16 and the tibial nerve 17 extend up to toes of the human body 1 (a first toe 18 (big toe), a second toe 19, a third toe 20, a fourth toe 21 and a fifth toe 22 (little toe)) as terminal portions of the ischiadic nerve 15. That is, the peroneal nerve 16 and the tibial nerve 17 of the toes 18 to 22 are connected by way of the ischiadic nerve 15 to the hypogastric nerve 12, the pelvic nerve 13 and the pudic nerve 14.

Next, a description will be given of a configuration and operation of the urination disorder treatment device 31 according to the first preferred embodiment of the present invention.

First Preferred Embodiment

Figure 4:
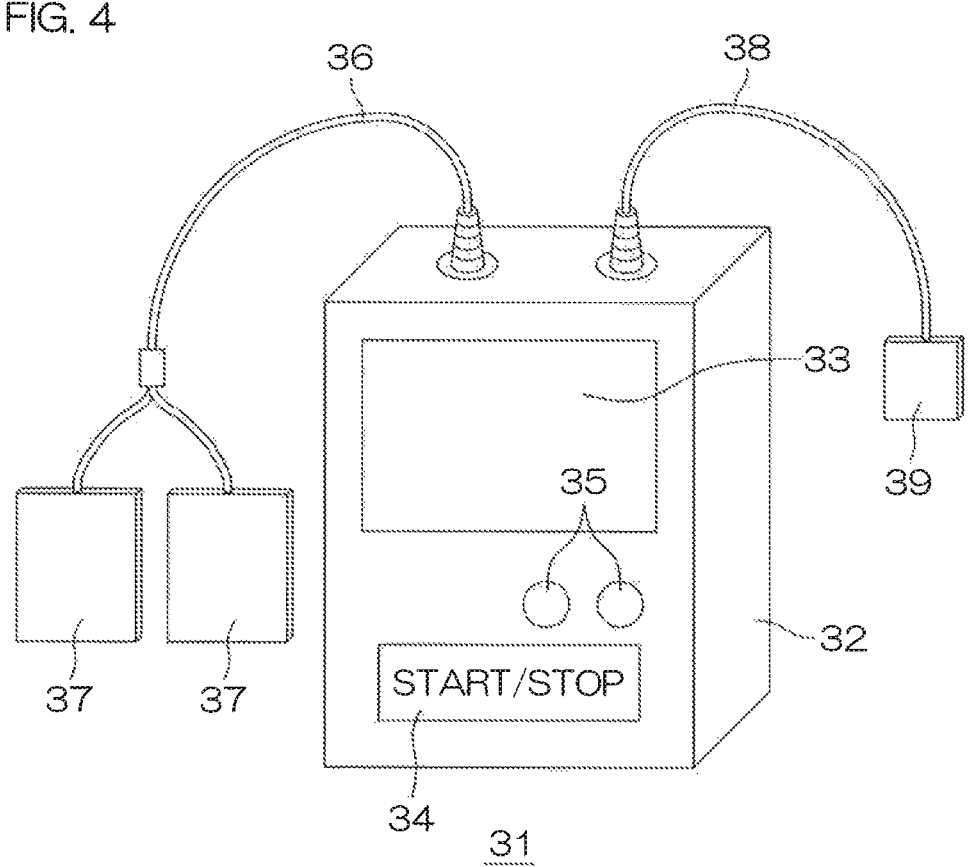
FIG. 4 is a schematic diagram of a urination disorder treatment device according to the first preferred embodiment of the present invention.

FIG. 4 is a schematic view of the urination disorder treatment device 31 according to the first preferred embodiment of the present invention.

The urination disorder treatment device 31 is physically arranged with a body 32, a monitor 33 placed on a front surface of the body 32, a start/stop button 34 and a plurality of operation buttons 35, 35 which are placed below the monitor 33, a pair of body-surface electrode pads 37 which is connected to the body 32 byway of a wiring 36, as an example of the application electrodes of the present invention, and a toe-use electrode pad 39 which is connected to the body 32 by way of a wiring 38, as an example of the detection electrode of the present invention.

The body 32 may be, for example, a plastic-made case. Further, although not shown in the drawing, at the back of the body 32, there may be provided a removable back lid for housing a battery for a power source of the urination disorder treatment device 31. The power source of the urination disorder treatment device 31 may not necessarily be a battery but may be obtained, for example, from an electrical outlet by way of an AC adaptor. Alternatively, the battery may be used together with the outlet.

The monitor 33 may be, for example, a black-and-white or color liquid crystal monitor. On the monitor 33, there can be displayed, for example, a pulse waveform and a frequency of an electrical stimulation signal by the body-surface electrode pad 37, an electrocardiographic waveform and a heart rate of a person to be treated, an error message and others. Thereby, the person to be treated is able to easily know the operating state of the urination disorder treatment device 31.

The operation button 35 may have various functions depending on a type of the urination disorder treatment device 31. For example, as a memory function of the urination disorder treatment device 31, a treatment menu including a width of a pulse wave (pulse width), a frequency of a stimulation signal, suitable for each of a plurality of persons to be treated is stored in the urination disorder treatment device 31, and the button, etc., that is operated in reading a treatment menu may be provided.

As the body-surface electrode pad 37 and the toe-use electrode pad 39, for example, a publicly-known adhesive gel pad, etc., may be used.

In using the urination disorder treatment device 31, at first, a person to be treated attaches the body-surface electrode pad 37, for example, on the skin immediately above the back of the sacral bone of the person. The operation button 35 is used to select a treatment menu suitable for the person, and the start/stop button 34 is pushed. Thereby, an electrical stimulation signal is output from the body-surface electrode pad 37 to stimulate the third sacral nerve S3. Then, it is possible to start the treatment by the urination disorder treatment device 31. Conditions of the stimulation signal (output pulse) may be, for example, 1 µs (second) to 500 µs (second) of the pulse width and 1 Hz to 50 Hz of the pulse frequency.

On the other hand, the toe-use electrode pad 39 may be attached to a toe as a detection electrode for confirming (monitoring) whether or not the stimulation signal from the body-surface electrode pad 37 is appropriately delivered to the pelvic nerve 13 and the pudic nerve 14. The toe to which the toe-use electrode pad 39 is attached may be any one of the first toe 18 to the fifth toe 22. However, the first toe 18 is preferable in view of easy attachment.

Next, a detailed description will be given of "processing related to stimulation influence elimination on the heart" and "processing on monitoring of a stimulation site" executed by the urination disorder treatment device 31, together with an electrical configuration of the urination disorder treatment device 31.

Figure 5:
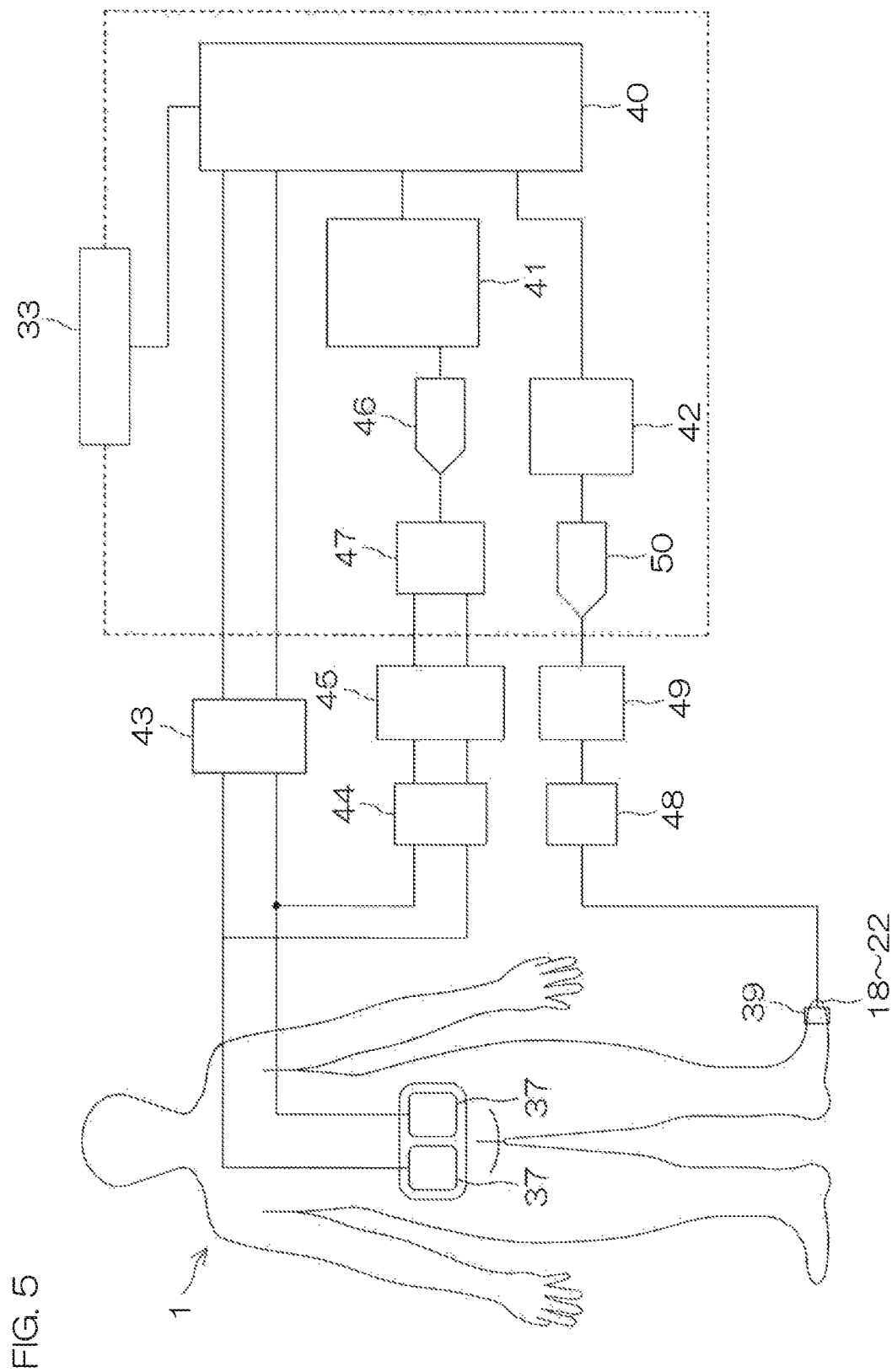
FIG. 5 is a block diagram which shows an electrical configuration of the urination disorder treatment device in FIG. 4.

FIG. 5 is a block diagram which shows an electrical configuration of the urination disorder treatment device 31 in FIG. 4.

The urination disorder treatment device 31 includes, as an electrical configuration, a control portion 40, a first measurement portion 41 for measuring electrocardiographic data of a person to be treated, a second measurement portion 42 which measures electromyographic data of the toes of the person to be treated, and a stimulation signal control output circuit 43 as an example of the signal supply source of the present invention which outputs a stimulation signal to the person to be treated under conditions based on control of the control portion 40. The control portion 40, the first measurement portion 41 or the second measurement portion 42 may be arranged as a microcomputer which includes, for example, a CPU, memories such as ROM and RAM and a timer.

The first measurement portion 41 and the stimulation signal control output circuit 43 are connected in parallel between the body-surface electrode pad 37 and the control portion 40. That is, the first measurement portion 41 measures the electrocardiographic data of a person to be treated by the body-surface electrode pad 37 from which a signal from the stimulation signal control output circuit 43 is output. For example, an input protection circuit 44, a signal amplifying circuit 45, an A/D converting circuit 46, etc., may be provided between the first measurement portion 41 and the body-surface electrode pad 37. In addition, a selector switch 47 for selecting output of the signal amplifying circuit 45 which is input to the A/D converting circuit 46 may be provided between the signal amplifying circuit 45 and the A/D converting circuit 46. The selector switch 47 is to output a plurality of signals as a single signal.

The second measurement portion 42 is connected between the control portion 40 and the toe-use electrode pad 39. For example, an input protection circuit 48, a signal amplifying circuit 49, an A/D converting circuit 50 and others may also be provided between the second measurement portion 42 and the toe-use electrode pad 39.

The control portion 40 is connected to the monitor 33, and contents of processing at the control portion 40 are displayed on the monitor 33, whenever necessary.

<Processing Related to Stimulation Influence Elimination on the Heart>

Figure 6:
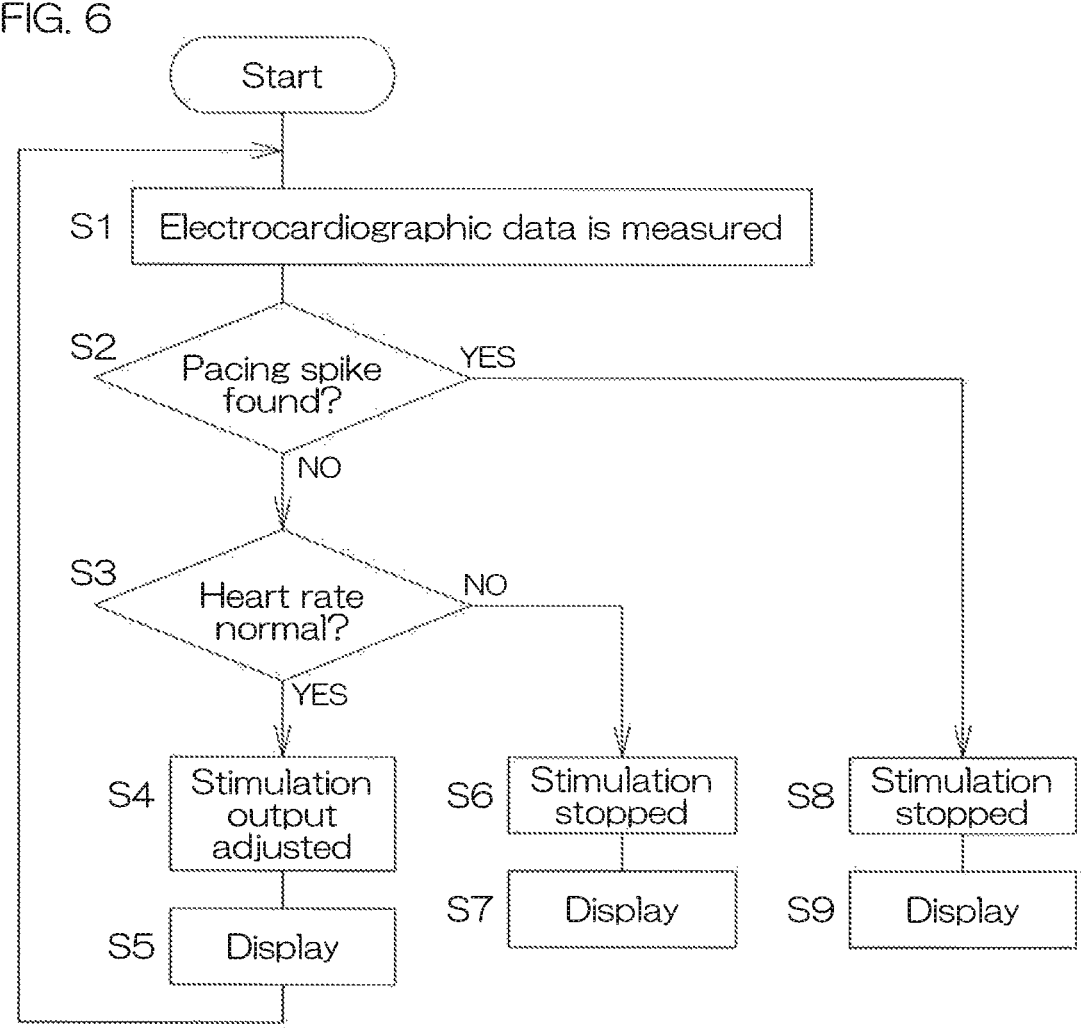
FIG. 6 is a flow chart which describes one example of processing related to stimulation influence elimination on the heart that is executed by a control portion.
Figure 7:
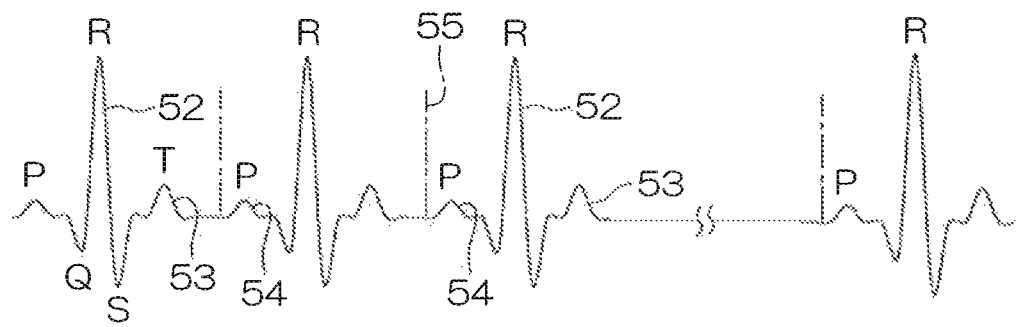
FIG. 7 is a drawing which describes one example of an electrocardiographic waveform measured by the measurement portion.
Figure 8:
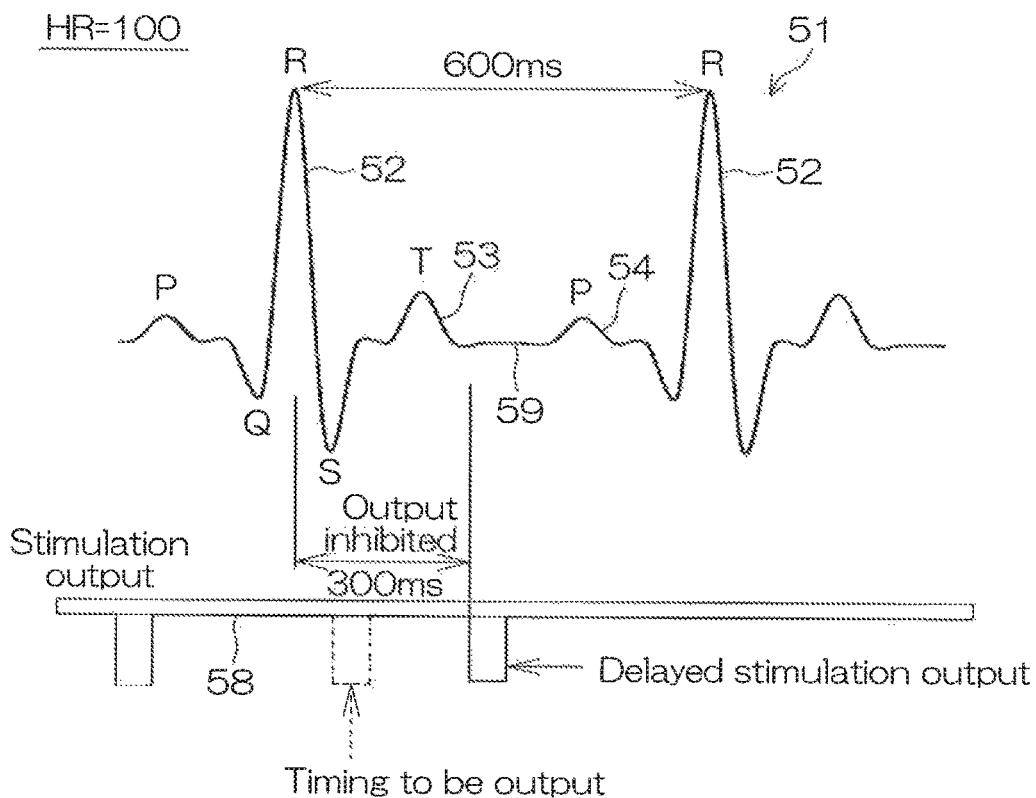
FIG. 8 is a drawing which describes one example of output timing of a stimulation pulse.
Figure 9:
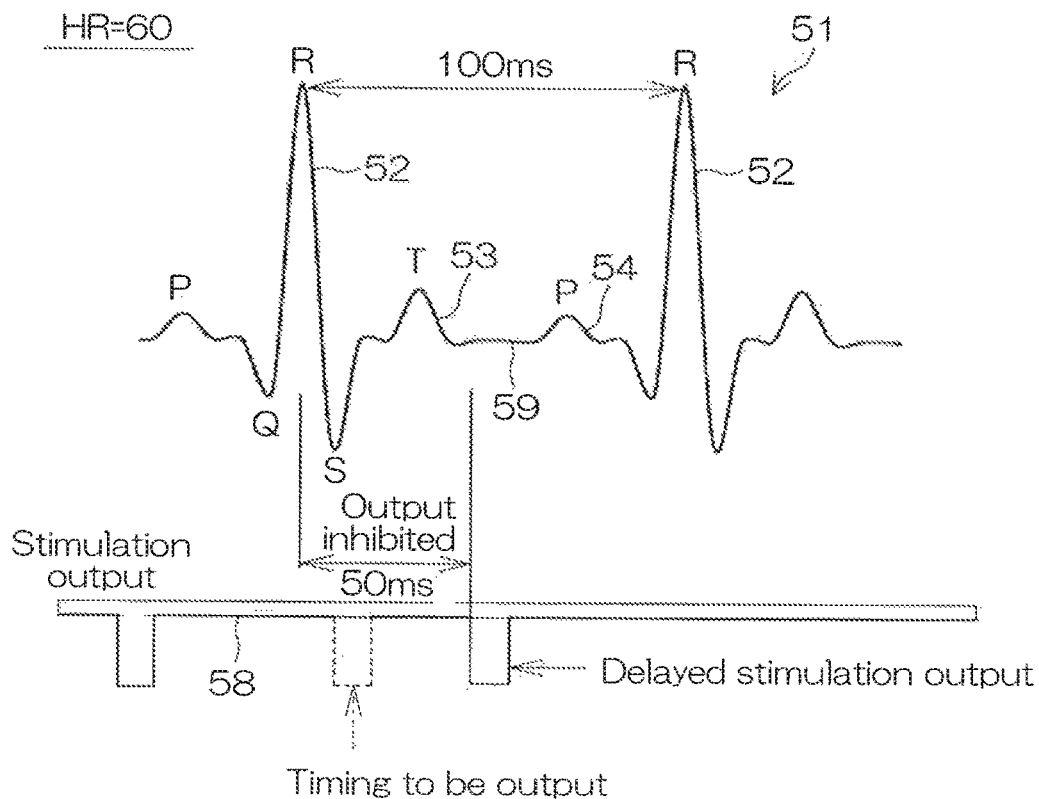
FIG. 9 is a drawing which describes one example of output timing of the stimulation pulse.

FIG. 6 is a flow chart which describes an example of the processing related to stimulation influence elimination on the heart which is executed by the control portion 40. FIG. 7 is a drawing which describes an example of electrocardiographic waveforms measured by the first measurement portion 41. FIG. 8 and FIG. 9 are each a drawing which describes an example of the timing of outputting a stimulation pulse.

As described above, when a user pushes the start/stop button 34 to start the treatment by the urination disorder treatment device 31, there is a case that electrocardiographic data may be detected by the first measurement portion 41 depending on a position at which the body-surface electrode pad 37 is attached, although no electrocardiographic data is detected if the body-surface electrode pad 37 is attached appropriately. At this time, for example, as shown in FIG. 6, the electrocardiographic data is measured by the first measurement portion 41 (Step S1). More specifically, based on signals of electrical activity of the heart of a person to be treated which are obtained from the pair of body-surface electrode pads 37 (one of them is a positive (+) electrode and the other is a negative (−) electrode), the electrocardiographic data of the person to be treated is measured by the first measurement portion 41. Thereby, for example, an electrocardiographic waveform 51 shown in FIG. 7 is prepared. The electrocardiographic waveform 51 in FIG. 7 includes, for example, a QRS wave 52, a T wave 53 and a P wave 54.

Next, a judgment is made for whether a signal of pacing spike 55 is found in the obtained electrocardiographic waveform 51 or not (Step S2). Where no pacing spike 55 is found (NO in Step S2), next, a heart rate of the person to be treated is measured based on the electrocardiographic waveform 51. The heart rate can be calculated, for example, with reference to a length between peaks 56 of the QRS waves 52 or a length between peaks 57 of the P waves 54 in the electrocardiographic waveform 51.

Next, where the heart rate is normal (for example, 60 to 100 beats per minute) (YES in Step S3), stimulation output is controlled to delay the timing of output from the pair of body-surface electrode pad 37 so as not to be synchronized with the atrial systole P or the ventricular systole R of the electrocardiographic data (Step S4).

More specifically, as shown in FIG. 8, where a length between the peaks 56 of the QRS waves 52 in the electrocardiographic waveform 51 is 600 ms and where the calculated heart rate is 100, 300 ms from the peak 56 of the QRS wave 52 is given as an output inhibition period, and a pulse 58 of the stimulation output is controlled so as to be later than the QRS wave 52 and the T wave. Further, as shown in FIG. 9, where a length between the peaks 56 of the QRS waves 52 in the electrocardiographic waveform 51 is 100 ms and where the calculated heart rate is 60, 50 ms from the peak 56 of the QRS wave 52 is given as an output inhibition period and a stimulation pulse 58 is controlled so as to be later than the QRS wave 52 and the T wave. Thereby, the stimulation pulse 58 is output when the electrocardiographic waveform 51 is in a state of equipotential line 59, and an electrical stimulation is given to the sacral plexus from the pair of body-surface electrode pads 37.

Next, as shown in FIG. 8 and FIG. 9, an image obtained by comparing the electrocardiographic waveform 51 with the stimulation pulse 58 is displayed on the monitor 33 (Step S5). Thereby, a person to be treated is able to know his/her own electrocardiographic waveform 51 and the timing at which the stimulation pulse 58 is output to the electrocardiographic waveform 51.

On the other hand, where, as a result of measurement of the heart rate based on the electrocardiographic waveform 51, there is found bradycardia with the heart rate lower than a normal rate or tachycardia with the heart rate higher than a normal rate (NO in Step S3), stimulation from the pair of body-surface electrode pads 37 is automatically stopped (Step S6). Then, an error message, for example, "the treatment has been stopped due to a low (or high) heart rate" is displayed on the monitor 33 together with the heart rate (Step S7).

Further, where appearance of the pacing spike 55 (refer to FIG. 7) in the electrocardiographic waveform 51 has been judged after preparation of the electrocardiographic waveform 51 (YES in Step S2), stimulation from the pair of body-surface electrode pads 37 is automatically stopped (Step S8). Then, an error message, for example, "the treatment has been stopped due to use of a pacemaker" is displayed on the monitor 33 (Step S9).

As described so far, according to the urination disorder treatment device 31, for example, even where the body-surface electrode pad 37 is attached to a site relatively close to the heart and an electrical stimulation from the urination disorder treatment device 31 is accidentally turned on, the above-described processing is executed immediately by detection of the electrocardiographic data. That is, supply of the stimulation signal supplied from the pair of body-surface electrode pads 37 will be stopped (Steps S6, S8) or timing of the supply thereof will be adjusted (Step S4) so as not to influence electrical activity of the heart of a person to be treated. Thus, it is possible to suppress influences to the heart of the person to be treated by the urination disorder treatment device 31. As a result, it is possible to use the urination disorder treatment device 31 more safely than a conventional device.

<Processing on Monitoring of a Stimulation Site>

Figure 10:
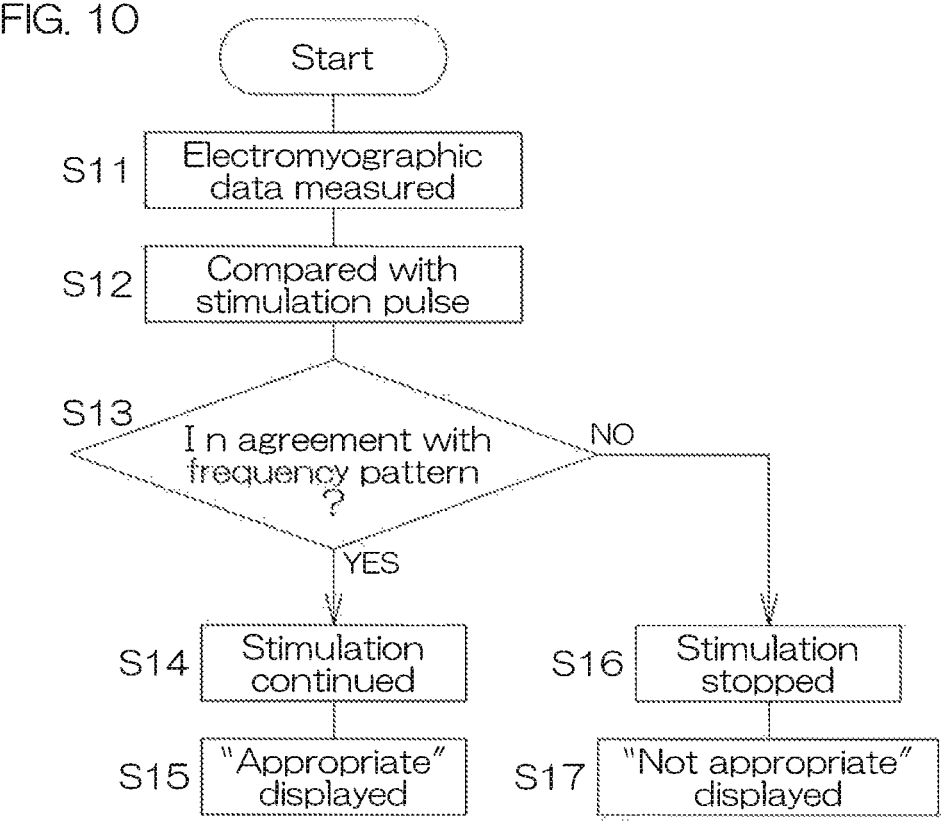
FIG. 10 is a flow chart which describes one example of processing on monitoring of a stimulation site that is executed by the control portion.
Figure 11:
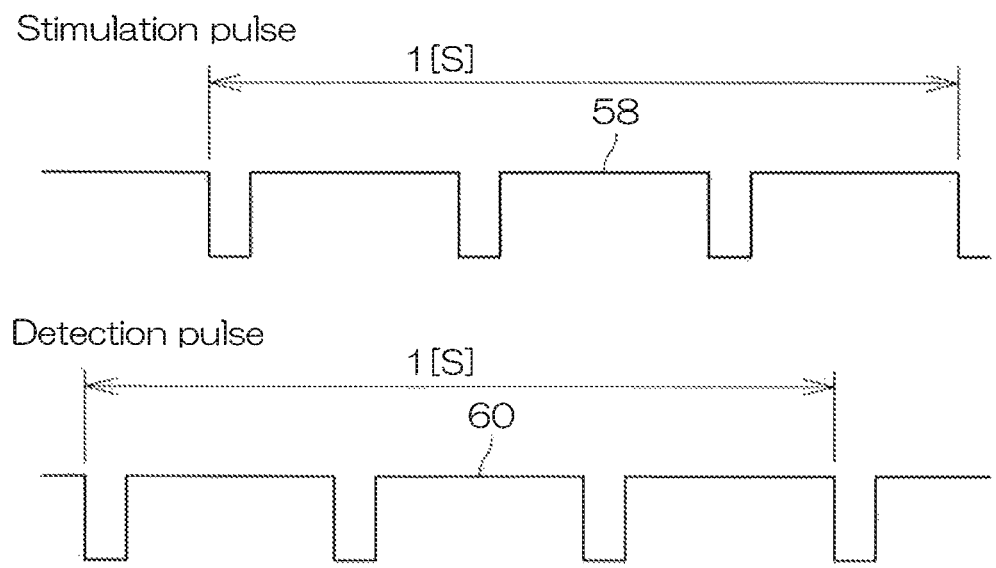
FIG. 11 is a drawing which describes one example of a frequency pattern of the stimulation pulse and that of a detection pulse.

FIG. 10 is a flow chart which describes an example of processing on confirmation of a stimulation site executed by the control portion 40. FIG. 11 is a drawing which describes an example of frequency patterns of a stimulation pulse and a detection pulse.

As described above, a user pushes the start/stop button 34 to start the treatment by the urination disorder treatment device 31. Unless the pair of body-surface electrode pads 37 are used by being attached to a predetermined position, no electrical stimulation is sufficiently given to the sacral plexus, thereby reducing effects of the treatment.

Thus, in the urination disorder treatment device 31, the toe-use electrode pad 39 attached to the toes 18 to 22 is used to detect minute myoelectricity resulting from muscular activity of the toes 18 to 22, and electromyographic data of the toes 18 to 22 is prepared (Step S11).

Next, as shown in FIG. 11, the stimulation pulse 58 is compared with a detection pulse 60 of the electromyographic data (Step S12). Where an electrical stimulation by the pair of body-surface electrode pads 37 is given, for example, to the third sacral nerve S3, only at the timing when the stimulation is given, myoelectricity is detected to obtain electromyographic data at terminal portions of the peroneal nerve 16 and the tibial nerve 17 present in the toes 18 to 22. Therefore, if a frequency pattern of the stimulation pulse 58 is in agreement with a frequency pattern of the detection pulse 60, it is judged that the pair of body-surface electrode pads 37 are attached at appropriate positions to give an electrical stimulation (YES in Step S13). The electrical stimulation is continuously applied by the pair of body-surface electrode pads 37 (Step S14) and the fact that pads are attached at appropriate positions is displayed on the monitor 33 (Step S15).

On the other hand, where the pair of body-surface electrode pads 37 are not attached to the skin immediately above the sacral bone 3 but attached to the femur of a person to be treated, for example, a position farther away from the sacral bone 3, myoelectricity is detected (detected at a different frequency pattern) even at the timing when no stimulation is given or no myoelectricity is detected at the timing when the stimulation is given. At this time, the health of a person to be treated may be adversely affected depending on a position at which the pair of body-surface electrode pads 37 are attached. For example, if the pair of body-surface electrode pads 37 are attached to a position close to the heart, the heart of the person to be treated may be affected by the stimulation.

Thus, where myoelectricity is detected even at the timing when no stimulation is given or no myoelectricity is detected at the timing when the stimulation is given (NO in Step S13), application of the electrical stimulation by the pair of body-surface electrode pads 37 is stopped (Step S16) and the fact that pads are not attached at appropriate positions is displayed on the monitor 33 (Step S17).

Monitoring of the electromyographic data can be described with reference to FIG. 12 and FIG. 13, in addition to the methods described with reference to FIG. 10 and FIG. 11.

Figure 12:
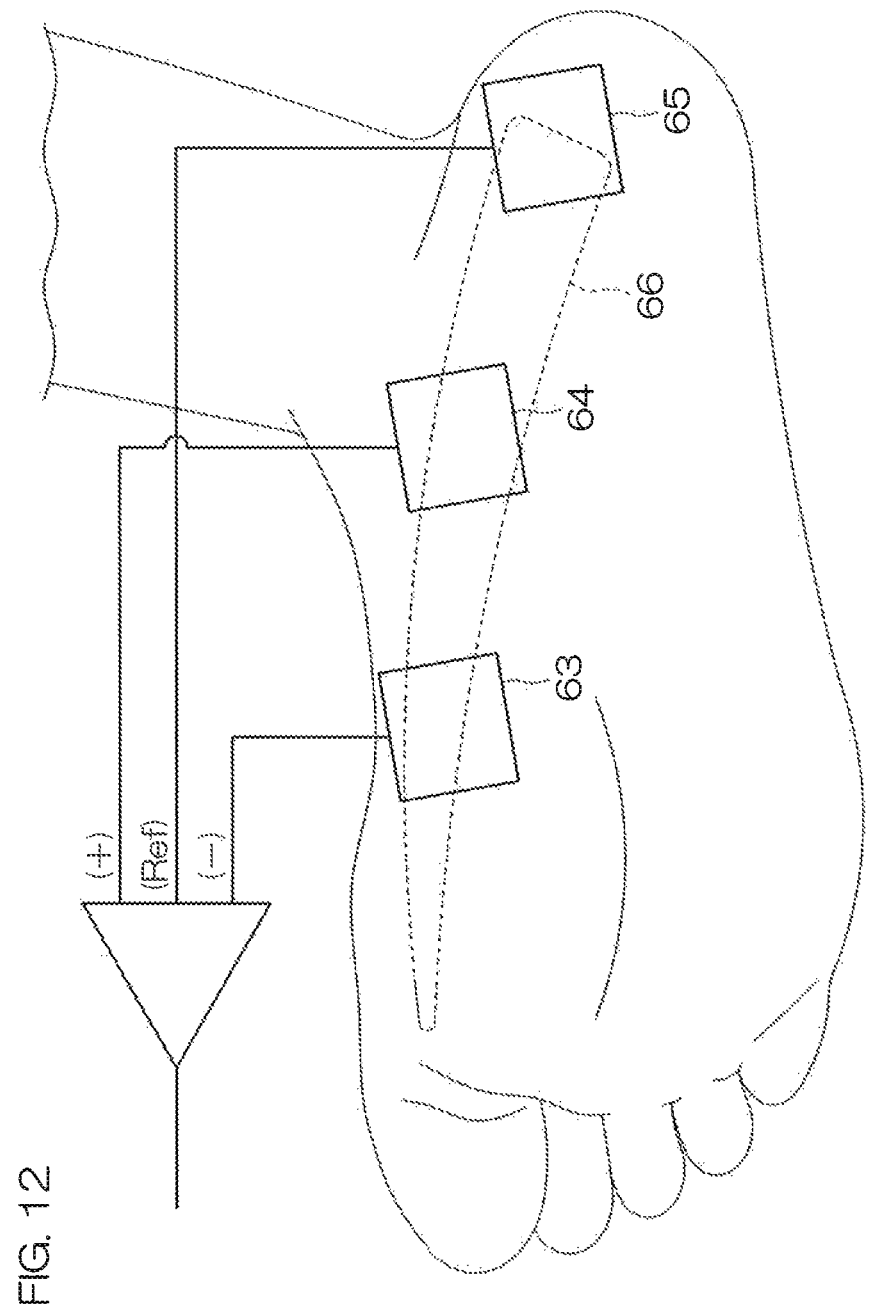
FIG. 12 is a drawing which shows an arrangement of electrode pads on monitoring of the electromyographic data.

FIG. 12 is a drawing which shows an arrangement of each of electrode pads 63 to 65 when the electromyographic data is monitored. FIG. 13 is a drawing which describes one example of frequency patterns of a stimulation pulse 61 and that of a detection pulse 62.

First, the toe-use electrode pad 39 of FIG. 5 may include a first electrode pad 63, a second electrode pad 64 and a third electrode pad 65, as shown in FIG. 12. In the preferred embodiment, the third electrode pad 65 may be a reference electrode, and the first electrode pad 63 may be a negative potential electrode (negative electrode) in relation to the third electrode pad 65. The second electrode pad 64 may be a positive potential electrode (positive electrode) in relation to the third electrode pad 65.

The first electrode pad 63, the second electrode pad 64 and the third electrode pad 65 may be adhered, for example, so as to face muscle fibers of an abductor hallucis muscle 66 along a direction at which the muscle fibers of the abductor hallucis muscle 66 of the toe are extended, that is, according to the above-described order from the tiptoe. The abductor hallucis muscle 66 is controlled by nerves connected to the peroneal nerve 16 and the tibial nerve 17 described above (for example, medial plantar nerves (L5 to S2)). Further, it is preferable that a distance between the first electrode pad 63 and the second electrode pad 64 and a distance between the second electrode pad 64 and the third electrode pad 65 are equal to each other.

Then, in order to conduct monitoring of the myoelectricity by using the first electrode pad 63, the second electrode pad 64 and the third electrode pad 65, for example, the stimulation pulse 61 shown in FIG. 13 is applied to the pair of body-surface electrode pads 37.

The stimulation pulse 61 may be continuously applied, for example, in a pattern which covers a rising portion $t_1=1$ second, a continuous part $t_2=1$ second, and a time interval up to a next pulse $t_3=1.5$ seconds, a total of 3.5 seconds. As a matter of course, lengths of $t_1$, $t_2$ and $t_3$, a magnitude of voltage and others may be adjusted according to the body size of a user, etc., whenever necessary.

Then, measurement data obtained by muscular contraction in association with the stimulation (for example, data covering 40 to 60 pulses) is averaged to remove noise, etc., thereby creating a waveform of electromyographic data (the waveform of detection pulse 62 shown in FIG. 13). Then, the waveform of the detection pulse 62 is compared with that of the stimulation pulse 61. If the patterns are the same, it is judged that the pair of body-surface electrode pads 37 are attached to an appropriate position to give an electrical stimulation. The pair of body-surface electrode pads 37 apply the electrical stimulation continuously and the fact that pads are attached appropriately is displayed on the monitor 33.

On the other hand, where the pattern of the stimulation pulse 61 is different from that of the detection pulse 62, application of the electrical stimulation by the pair of body-surface electrode pads 37 is stopped and the fact that pads are incorrectly attached is displayed on the monitor 33.

As described so far, the urination disorder treatment device 31 is able to easily confirm whether the stimulation signal is appropriately transmitted from the pair of body-surface electrode pads 37 to the nerves passing through the sacral bone or the vicinity of the sacral bone or not based on electromyographic data of the toes 18 to 22. Further, the toes 18 to 22 are terminal portions of the tibial nerve 17 and the peroneal nerve 16, and, therefore, noise is less likely to enter as compared with a case where a biological signal is detected at other parts of the human body 1, and a biological signal occurring in response to a stimulation signal can be clearly detected. Further, since the toes 18 to 22 are different from a site such as the perineum to which it is difficult to attach an electrode, the electrodes can be easily attached thereto. As a result, it is possible to confirm in a simplified manner with high accuracy whether the urination disorder treatment device 31 is appropriately used or not (whether the stimulation signal is appropriately transmitted or not).

One preferred embodiment of the present invention has been so far described. However, the present invention may be carried out in other modes.

Second Preferred Embodiment

For example, in the first preferred embodiment described above, a description has been given of a configuration of the urination disorder treatment device 31 which is a portable type. However, the electrical configuration and the control of the urination disorder treatment device shown in FIG. 5 to FIG. 11 may be applied to a stationary type urination disorder treatment device 31 in which a monitor is separated from a main body of the treatment device.

Third Preferred Embodiment

Further, in the first preferred embodiment described above, as an example of the display portion of the present invention, there is shown the monitor 33 which displays a message or an image for a user. However, a means for displaying an operating state of the urination disorder treatment device 31 for a user is not necessarily limited to the monitor 33. For example, a message to a person to be treated (for example, an error message or an incorrect position at which the electrode is attached) may be in advance printed on a front panel of the body 32 to illuminate characters thereof by using an LED, etc., or to switch on a lamp near the characters, so that the person to be treated can be informed.

Fourth Preferred Embodiment

Further, in the first preferred embodiment described above, an image obtained by comparing the electrocardiographic waveform 51 with the stimulation pulse 58 may not be displayed on the monitor 33.

Fifth Preferred Embodiment

Further, in the urination disorder treatment device 31 according to the first preferred embodiment described above, where the toe-use electrode pad 39 attached to the toes 18 to 22 is used to detect minute myoelectricity resulting from muscular activity of the toes 18 to 22 and prepare electromyographic data of the toes 18 to 22 (Step S1), myoelectricity obtained by the plurality of stimulation timings may be added and averaged to prepare the electromyographic data.

Sixth Preferred Embodiment

Further, in the first preferred embodiment described above, three patterns are shown as the processing related to stimulation influence elimination on the heart. However, for example, as shown in FIG. 14, at a stage that the electrocardiographic data is detected (YES in Step S21), stimulation is stopped (Step S22) and an error message may be displayed on the monitor 33 (Step S23). This method is a mode which can be used most safely.

Seventh Preferred Embodiment

Figure 15:
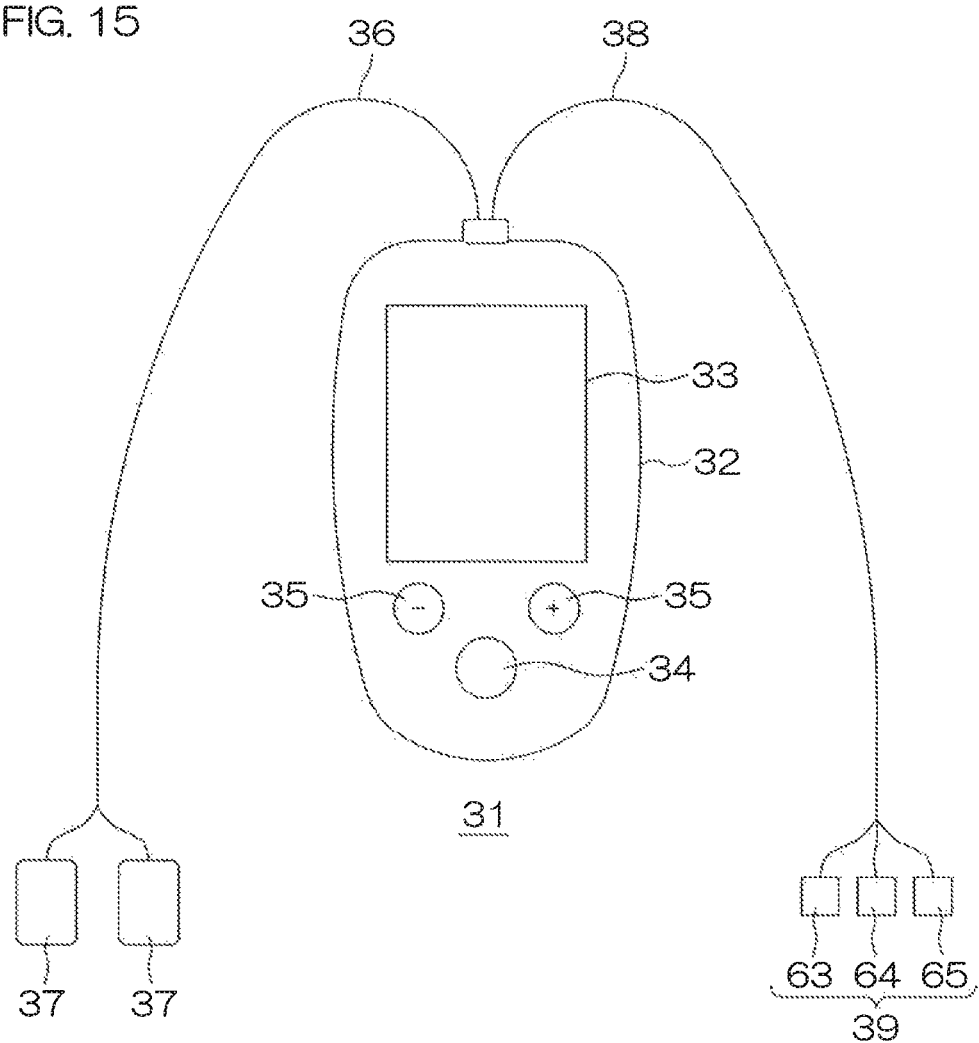
FIG. 15 is a drawing which describes another mode of the urination disorder treatment device.

Further, with reference to FIG. 15, the urination disorder treatment device 31 may be provided with a substantially oval-shaped body 32. The monitor 33 may be formed in a rectangular shape which is longer along a longitudinal direction of the body 32 and disposed so as to be closer to one end portion of the body 32 in the longitudinal direction. The start/stop button 34 and the plurality of operation buttons 35, 35 may be disposed on a side of the other end portion of the body 32 in the longitudinal direction in relation to the monitor 33.

In addition, the design of the present invention may be modified in various ways without departing from the scope described in the claims.

The present application corresponds to Japanese Patent Application No. 2017-171382 filed in the Japan Patent Office on Sep. 6, 2017, and the entire disclosure of this application is incorporated herein by reference.

REFERENCE SIGNS LIST

1: Human body
2: Vertebral column
3: Sacral bone
4: Lumbar vertebra
5: First sacral foramen
6: Second sacral foramen
7: Third sacral foramen
8: Fourth sacral foramen
9: Bladder
10: Internal urethral sphincter
11: External urethral sphincter
12: Hypogastric nerve
13: Pelvic nerve
14: Pudic nerve
15: Ischiadic nerve
16: Peroneal nerve
17: Tibial nerve
18: First toe (big toe)
19: Second toe
20: Third toe
21: Fourth toe
22: Fifth toe (little toe)
23: Control portion
24: First measurement portion
25: Second measurement portion
26: Stimulation signal control output circuit
31: Urination disorder treatment device
32: Body
33: Monitor
34: Start/stop button
35: Operation button
36: Wiring
37: Body-surface electrode pad
38: Wiring
39: Toe-use electrode pad
40: Control portion
41: First measurement portion
42: Second measurement portion
43: Stimulation signal control output circuit
44: Input protection circuit
45: Signal amplifying circuit
46: A/D converting circuit
47: Selector switch
48: Input protection circuit
49: Signal amplifying circuit
50: A/D converting circuit
51: Electrocardiographic waveform
52: QRS wave
53: T wave
54: P wave
55: Pacing spike
56: Peak of QRS wave
57: Peak of P wave
58: Stimulation pulse
59: Equipotential line
60: Detection pulse
61: Stimulation pulse
62: Detection pulse
63: First electrode pad
64: Second electrode pad
65: Third electrode pad

The invention claimed is:

1. A urination disorder treatment device comprising:
a pair of application electrodes which are disposed at the back of a sacral bone of a person to be treated to supply an electrical stimulation signal from the back of the sacral bone;
a signal supply source from which the pair of application electrodes supply the stimulation signal;
a detection electrode which is disposed on a surface of a toe of a person to be treated to detect a biological signal of the toe which is generated in response to the stimulation signal;
a measurement portion which is connected to the detection electrode to measure electromyographic data of the toe based on the biological signal of the toe of a person to be treated;
a control portion which is connected to the measurement portion to control supply of the stimulation signal to the sacral bone by the pair of application electrodes and also compares signal data of the stimulation signal with electromyographic data of the toe to judge whether a nerve which passes through the sacral bone or the vicinity of the sacral bone is appropriately stimulated by the stimulation signal or not; and
a display portion which informs a person to be treated of a judgment result by the control portion, wherein
the biological signal of the toe to be detected is generated by reactions of a tibial nerve and/or a peroneal nerve extended up to the tiptoe which are connected to a nerve passing through the sacral bone or the vicinity of the sacral bone by way of an ischiadic nerve, and
the control portion stop the stimulation signal when a frequency pattern of a pulse wave of the signal data of the stimulation signal has a different shape from that of a frequency pattern of a pulse wave of the electromyographic data by comparing the frequency pattern of the pulse wave of the signal data of the stimulation signal with the frequency pattern of the pulse wave of the electromyographic data.

2. The urination disorder treatment device according to claim 1, wherein the control portion stop the stimulation signal when no electromyographic data of the toe is detected even if the stimulation signal is supplied from the pair of application electrodes.

3. The urination disorder treatment device according to claim 1, wherein myoelectricity obtained by a plurality of timings of the stimulation signal are added and averaged to prepare the electromyographic data of the toe.

4. The urination disorder treatment device according to claim 1, wherein a fact that the pair of application electrodes are not attached at appropriate positions is displayed on the display portion when the frequency pattern of the pulse wave of the signal data of the stimulation signal has a different shape from that of the frequency pattern of a pulse wave of the electromyographic data.

5. The urination disorder treatment device according to claim 1, wherein
the detection electrode includes a first electrode, a second electrode and a third electrode,
the third electrode is a reference electrode,
the first electrode is a negative potential electrode in relation to the third electrode, and
the second electrode is a positive potential electrode in relation to the third electrode.

* * * * *